(12) United States Patent
Magen et al.

(10) Patent No.: US 12,023,516 B2
(45) Date of Patent: Jul. 2, 2024

(54) RADIOTHERAPY APPLICATOR

(71) Applicant: Alpha Tau Medical Ltd., Jerusalem (IL)

(72) Inventors: Ofer Magen, Hod Hasharon (IL); Or Zellner, Tel Aviv-Yaffo (IL); Sraya Makovsky, Beit Shemesh (IL); Itzhak Kelson, Tel Aviv (IL)

(73) Assignee: ALPHA TAU MEDICAL LTD., Jerusalem (IL)

( * ) Notice: Subject to any disclaimer, the term of this patent is extended or adjusted under 35 U.S.C. 154(b) by 0 days.

(21) Appl. No.: 18/263,716

(22) PCT Filed: Mar. 9, 2022

(86) PCT No.: PCT/IB2022/052084
§ 371 (c)(1),
(2) Date: Aug. 1, 2023

(87) PCT Pub. No.: WO2022/189987
PCT Pub. Date: Sep. 15, 2022

(65) Prior Publication Data
US 2024/0108913 A1 Apr. 4, 2024

Related U.S. Application Data

(60) Provisional application No. 63/159,499, filed on Mar. 11, 2021.

(51) Int. Cl.
*A61N 5/01* (2006.01)
*A61N 5/10* (2006.01)

(52) U.S. Cl.
CPC .... *A61N 5/1027* (2013.01); *A61N 2005/1011* (2013.01); *A61N 2005/1024* (2013.01)

(58) Field of Classification Search
CPC ................ A61N 5/1027; A61N 5/1007; A61N 2005/1011; A61N 2005/1024
See application file for complete search history.

(56) References Cited

U.S. PATENT DOCUMENTS

| 4,532,935 A | 8/1985 | Wang |
| 4,766,906 A | 8/1988 | Wang |

(Continued)

FOREIGN PATENT DOCUMENTS

| CN | 2647349 Y | 10/2004 |
| CN | 202036681 U | 11/2011 |

(Continued)

OTHER PUBLICATIONS

International Application # PCT/IB2022/052084 Search Report dated May 22, 2022.

(Continued)

*Primary Examiner* — Samuel G Gilbert
(74) *Attorney, Agent, or Firm* — KLIGLER & ASSOCIATES PATENT ATTORNEYS LTD.

(57) ABSTRACT

An applicator for delivery of radiotherapy seeds to a tumor of a patient through an elongate needle (104). The elongate needle comprises a needle handle (204) and a needle tube having a given length for insertion into the patient. The applicator comprises an elongate applicator tube (106) designed to pass through the elongate needle, wherein the elongate applicator tube defines an internal channel which receives one or more radiotherapy seeds (110), an applicator handle (210) configured to be attached to the needle handle (204); and a stylet (108) within the elongate applicator tube. The elongate applicator tube is longer than the elongate needle.

9 Claims, 8 Drawing Sheets

(56) References Cited

U.S. PATENT DOCUMENTS

| | | | |
|---|---|---|---|
| 4,997,424 A | 3/1991 | Little | |
| 6,159,143 A | 12/2000 | Lennox | |
| 6,210,315 B1 | 4/2001 | Andrews et al. | |
| 6,213,932 B1 | 4/2001 | Schmidt | |
| 6,264,600 B1 | 7/2001 | Grimm | |
| 6,270,472 B1 * | 8/2001 | Antaki | A61M 37/0069 600/7 |
| 6,752,753 B1 * | 6/2004 | Hoskins | A61N 5/1007 600/7 |
| 7,041,047 B2 | 5/2006 | Gellman et al. | |
| 8,365,721 B2 | 2/2013 | Larsen et al. | |
| 8,795,145 B2 | 8/2014 | Hermann et al. | |
| 8,834,837 B2 | 9/2014 | Kelson et al. | |
| 10,543,379 B2 | 1/2020 | Hingston et al. | |
| 2003/0199726 A1 | 10/2003 | Gatto | |
| 2003/0220533 A1 | 11/2003 | Pedersen et al. | |
| 2005/0038312 A1 | 2/2005 | Green et al. | |
| 2005/0209499 A1 | 9/2005 | Elliott et al. | |
| 2006/0085068 A1 | 4/2006 | Barry | |
| 2007/0055172 A1 | 3/2007 | Ratnakar | |
| 2008/0207982 A1 | 8/2008 | Elliott et al. | |
| 2009/0112161 A1 | 4/2009 | Maerten et al. | |
| 2009/0112261 A1 | 4/2009 | Barry | |
| 2009/0136422 A1 | 5/2009 | Kelson et al. | |
| 2009/0193764 A1 | 8/2009 | Elliott et al. | |
| 2009/0234176 A1 | 9/2009 | Lebovic et al. | |
| 2010/0280494 A1 | 11/2010 | Matsuura et al. | |
| 2010/0292711 A2 | 11/2010 | Selis | |
| 2011/0257459 A1 | 10/2011 | Sutton et al. | |
| 2013/0204124 A1 | 8/2013 | Duindam et al. | |
| 2014/0121445 A1 | 5/2014 | Fontenot et al. | |
| 2015/0273207 A1 | 10/2015 | Tran et al. | |
| 2015/0273237 A1 | 10/2015 | Raus et al. | |
| 2016/0136454 A1 * | 5/2016 | Kader | A61N 5/1007 600/7 |
| 2018/0296855 A1 | 10/2018 | Lohrenz et al. | |
| 2018/0345038 A1 * | 12/2018 | Kelson | A61N 5/1015 |
| 2020/0086140 A1 | 3/2020 | Stoianovici et al. | |
| 2020/0101049 A1 | 4/2020 | Seward | |
| 2020/0146757 A1 | 5/2020 | Fenech et al. | |
| 2020/0261740 A1 | 8/2020 | Baker et al. | |
| 2020/0345980 A1 | 11/2020 | Serina et al. | |
| 2020/0406059 A1 * | 12/2020 | Kelson | A61L 2/04 |
| 2021/0145445 A9 | 5/2021 | Goldsmith | |
| 2021/0146154 A1 | 5/2021 | Racenet et al. | |
| 2022/0117468 A1 | 4/2022 | Barry et al. | |
| 2022/0142500 A1 | 5/2022 | Greenburg et al. | |
| 2023/0001232 A1 | 1/2023 | Magen et al. | |

FOREIGN PATENT DOCUMENTS

| | | |
|---|---|---|
| CN | 202961502 U | 6/2013 |
| CN | 203898926 U | 10/2014 |
| CN | 111249612 A | 6/2020 |
| CN | 111632261 A | 9/2020 |
| CN | 215781051 U | 2/2022 |
| EP | 3708581 A1 | 9/2020 |
| JP | H0394773 A | 4/1991 |
| KR | 20140016030 A | 2/2014 |
| RO | 134941 A2 | 5/2021 |
| WO | 03039463 A2 | 5/2003 |
| WO | 2011053908 A1 | 5/2011 |
| WO | 2015136192 A1 | 9/2015 |
| WO | 2020188508 A1 | 9/2020 |
| WO | 2022189987 A1 | 9/2022 |
| WO | 2022/259166 A1 | 12/2022 |

OTHER PUBLICATIONS

U.S. Appl. No. 17/852,610 Office Action dated Jan. 29, 2024.
U.S. Appl. No. 17/852,610 Office Action dated Mar. 28, 2024.

* cited by examiner

RADIOTHERAPY APPLICATOR

CROSS-REFERENCE TO RELATED APPLICATION

This application claims the benefit of U.S. Provisional Patent Application 63/159,499, filed Mar. 11, 2021, which is incorporated herein by reference.

FIELD OF THE INVENTION

The present invention relates generally to radiotherapy and particularly to methods of implanting radiotherapy sources in tumors located in internal organs.

BACKGROUND OF THE INVENTION

Alpha particle emitters are a powerful means for radiotherapy of certain types of tumors, including malignant tumors. Proper delivery of seeds with embedded alpha particle emitters is important to the success of the therapy. The delivery should accurately position the seeds inside the tumor, without premature exposure of tissue of the patient and others to radioactive and otherwise unhealthy substances.

One type of alpha radiotherapy sources is diffusing alpha-emitter radiation therapy (DaRT) sources loaded with radium-223 or radium-224 atoms, which have a half-life which is not too long and not too short for therapeutic purposes.

U.S. Pat. No. 8,834,837 to Kelson describes a method of DaRT treatment.

PCT publication WO2015/136192, titled: "Brachytherapy Device and Associated Therapeutic Method" describes delivery of containers of a radioactive substance through a needle inserted into a channel of an endoscope.

U.S. Pat. No. 4,532,935 to Wang, describes a bronchoscopic needle including an outer catheter, a needle attached to an inner catheter, inside the outer catheter, and a stylet which passes within the needle.

SUMMARY OF THE INVENTION

There is herein provided in accordance with embodiments of the invention, an applicator for delivery of radiotherapy seeds to a tumor of a patient through an elongate needle, wherein the elongate needle comprises a needle handle and a needle tube having a given length for insertion into the patient, comprising:
  an elongate applicator tube designed to pass through the elongate needle, wherein the elongate applicator tube defines an internal channel which receives one or more radiotherapy seeds;
  an applicator handle configured to be attached to the needle handle; and
  a stylet within the elongate applicator tube,
  wherein the elongate applicator tube is longer than the elongate needle.

Optionally, the elongate applicator tube has a flexibility which is not suitable for insertion into a patient, but can pass through an inner channel of the elongate needle, when the elongate needle is in the patient. Optionally, the elongate applicator tube has a length such that when the applicator handle is attached to the needle handle, a distal end of the elongate applicator tube is in close proximity to a distal end of the elongate needle. Optionally, the elongate applicator tube has a length of at least 20 centimeters. Optionally, the applicator further comprises a seed dispensing unit configured to grasp the applicator handle and a handle of the stylet, in a manner which allows movement of the applicator handle relative to the stylet handle, such that the stylet pushes a seed out of the distal end of the elongate applicator tube. Optionally, the seed dispensing unit comprises a casing configured to grasp the stylet handle; and a slidable holder configured to couple with the applicator handle and slide relative to the casing.

Optionally, the seed dispensing unit comprises a guide handle which when moved, by a user, along an axis of the elongate applicator tube, moves the applicator handle relative to the stylet handle. Optionally, the seed dispensing unit is configured to limit movement of the guide handle along the axis of the elongate applicator tube in a single stroke, to the length of a single seed. Optionally, the seed dispensing unit is configured to require sideways movement of the guide handle, to allow further movement of the guide handle along the axis of the elongate applicator tube, after movement of the length of a single seed. Optionally, the seed dispensing unit is configured to retract the applicator handle while the handle of the stylet is held in place. Optionally, the elongate applicator tube has a length of at least 50 centimeters.

There is further provided in accordance with embodiments of the invention, a seed dispensing unit, comprising:
  an applicator handle holder configured to grasp a handle of an elongate applicator including a plurality of radiotherapy seeds at its distal end;
  a stylet handle grasper configured to grasp a handle of a stylet in the elongate applicator; and
  a casing configured to allow motion of the applicator handle holder relative to the stylet handle grasper, such that the stylet pushes a seed out of the distal end of the elongate applicator, wherein the casing is configured to limit uninterrupted motion of the applicator handle holder relative to the stylet handle grasper to the length of a single seed, such that further motion is allowed only after an adjustment action by a human user.

Optionally, the applicator handle holder comprises a guide handle used by the user to move the applicator handle holder relative to the stylet handle grasper in a first direction, and wherein the casing requires movement in a second direction, different from the first direction, in order to move in the first direction beyond the length of a single seed. Optionally, the second direction is perpendicular to the first direction. Optionally, the applicator handle holder comprises a ratchet which prevents backward movement of the applicator handle holder after it is moved the length of a seed, unless a ratchet release button is pressed. Optionally, the casing comprises one or more ball plungers, which limit uninterrupted motion of the applicator handle holder relative to the stylet handle grasper to the length of a single seed.

There is further provided in accordance with embodiments of the invention, a system for delivery of radiotherapy seeds to a tumor, comprising an endoscope defining an elongate channel, an elongate needle which passes through the elongate channel of the endoscope, an elongate applicator which passes through the elongate needle, and defines an internal channel which receives one or more radiotherapy seeds, and a stylet within the elongate applicator.

Optionally, the system comprises a seed dispensing unit configured to receive a handle of the needle on one end and a handle of the stylet on an opposite end. Optionally, the seed dispensing unit includes a needle handle holder configured to hold the needle handle and a proximal compartment which receives the handle of the stylet. Optionally, the seed dispensing unit is configured to push the needle handle holder towards the proximal compartment by fixed lengths, sufficient to dispense a single seed from the applicator.

There is further provided in accordance with embodiments of the invention, a method of delivering radiotherapy seeds to an internal organ of a patient, comprising:

providing an elongate applicator of a length sufficient to extend from outside the patient to the internal organ, wherein the elongate applicator includes one or more radiotherapy seeds at its distal end and a stylet running through the elongate applicator from its proximal end to the one or more radiotherapy seeds;

inserting the elongate applicator into an elongate needle;

perforating a hole in the internal organ by the elongate needle; and dispensing at least one of the seeds in the patient by retracting the elongate needle and the elongate applicator relative to the stylet.

Optionally, inserting the elongate applicator into the elongate needle is performed while the elongate needle extends from outside the patient to the internal organ. Optionally, inserting the elongate applicator into the elongate needle is performed while the elongate needle is entirely outside the patient. Optionally, the method includes leading the needle to a proximity of the organ through an endoscope. Optionally, the method includes connecting a handle of the needle to a handle of the applicator before dispensing the at least one of the seeds.

DETAILED DESCRIPTION OF EMBODIMENTS

An aspect of some embodiments of the present invention relates to delivery of radiotherapy seeds to an internal organ of a patient, within three tubes, one inside the other, which each can be manipulated separately. The delivery of the radiotherapy seeds within three tubes increases the flexibility of the delivery. In some embodiments, the outer tube is an endoscope, the intermediate tube an elongate needle and the inner tube is an applicator which carries the seeds. The use of the elongate needle in addition to the endoscope allows using the properties of the endoscope, such as sturdiness and visibility, to reach the vicinity of a tumor, while using the additional flexibility and the smaller diameter of the elongate needle to reach the tumor itself. Using an elongate applicator, separate from the elongate needle, to carry the seeds, allows delivery of the seeds to the distal end of the elongate needle, while the elongate needle is in the patient, without passing the seeds within an internal channel of the elongate needle, in a manner which may rub the seeds against internal walls of the elongate needle. As some radiotherapy seeds have their active radioactive particles on their outer surface, passing the seeds in an inner channel of the elongate needle could cause the seeds to lose a substantial portion of their activity due to the rubbing of the seeds against the inner walls of the elongate needle. The separate insertion of the elongate applicator may allow for delivery of additional seeds to the tumor, beyond the seeds originally loaded to the elongate needle. In addition, the use of the elongate applicator allows delivery of the distal end of the elongate needle to the tumor without the seeds therein, allowing for further flexibility of the elongate needle, when necessary.

An aspect of some embodiments of the present invention relates to a system for delivery of seeds to an internal organ of a patient, including two elongate tubes of about the same length, of which one fits into the other. Optionally, each of the elongate tubes has a handle and the handles are configured to be coupled to each other in a manner that the distal ends of the elongate tubes are in close proximity to each other when the handles are coupled. In some embodiments, the inner tube carries one or more radiotherapy seeds and a stylet which is used to push the seeds out of the distal end of the applicator.

Figure 1:
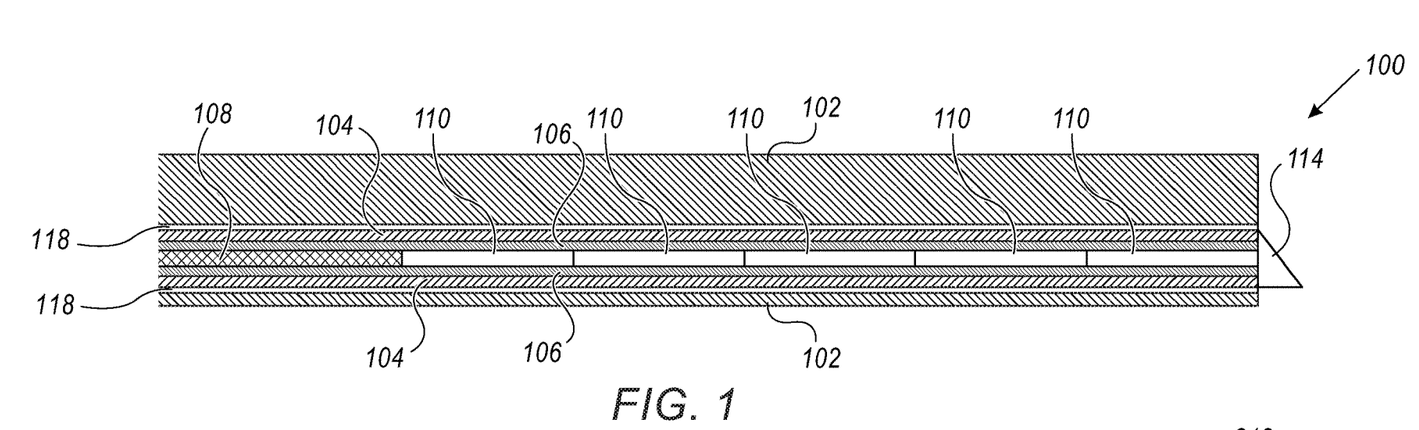
FIG. 1 is a partial cross section of a system for delivering radiotherapy seeds, in accordance with an embodiment of the present invention.

FIG. 1 is a partial cross section of a system 100 for delivering one or more radiotherapy seeds 110 to a location in a patient, in accordance with an embodiment of the invention. System 100 comprises a endoscope 102 suitable for insertion into a patient. An elongate needle 104 having a sharp edge 114 (shown schematically in FIG. 1), such as used in the art for taking biopsies, is inserted through a channel of the endoscope 102. Elongated needle 104 optionally comes with an outer sheath 118 in which elongate needle 104 may slide, between a delivery state in which sharp edge 114 is entirely within the sheath 118 and an operative state in which sharp edge 114 is outside the sheath, as shown in FIG. 1.

An applicator 106, carrying seeds 110 therein, passes through needle 104. A stylet 108 within applicator 106 is used to push seeds 110 into the patient. As shown, applicator 106 carries five seeds 110, which generally each has a length of between 0.5-2 centimeters. It is noted that applicator 106 may carry fewer than five or even fewer than three seeds 110 or may carry more than five or even more than ten seeds 110.

While needle 104 is shown inside a channel of the endoscope 102, in some cases the needle 104 may extend beyond the distal end of the endoscope and enter areas which are too narrow or are otherwise inaccessible by endoscope 102. Generally, therefore, at least a distal portion of elongate needle 104 is sufficiently stiff to allow independent maneuvering within a patient, while being sufficiently flexible to maneuver through twisted narrow body channels. In some embodiments, the elongate needle 104 has an outer diameter of less than 1.7 millimeters, less than 1.2 millimeters, or even less than 1 millimeter, for example 0.8 millimeters, and an inner diameter of less than 1.25 millimeters, less than 1 millimeter, less than 0.8 millimeters, or even less than 0.6 millimeters, for example 0.45 millimeters. Alternatively or additionally, elongate needle 104 has a relatively large outer diameter, for example greater than 1 millimeter, greater than 1.2 millimeters, or even greater than 1.5 millimeters.

In order to fit into elongate needle 104, applicator 106 has an outer diameter smaller than or equal to the inner diameter of elongate needle 104. The inner diameter of applicator 106 is sufficiently large to hold seeds 110, which optionally have a diameter greater than 0.3 millimeters, such as 0.37 millimeters. The wall of applicator 106 optionally has a thickness of less than 0.2 millimeters, less than 0.15 millimeters or even less than 0.1 millimeter. As applicator 106 is intended to pass through the inner channel of needle 104, in some embodiments, applicator 106 is very flexible in a manner which is not suitable for passage on its own within a patient. In addition, applicator 106 optionally has a high flexibility such that when located in needle 104, the combined flexibility of the needle 104 and applicator 106 still allows them to maneuver within the patient. Alternatively or additionally, when required to perform complex maneuvers, applicator 106 is removed from needle 104 and is returned when the needle is properly positioned. In some embodiments, applicator 106 comprises a braided or non-braided composite polyimide tube. Applicator 106 may also be removed from needle 104 in order to refill its distal end with seeds 110, and is reinserted into needle 104 after being refilled with the seeds. The elongate tube of applicator 106 is configured to be sufficiently stiff to allow for the removal and reinsertion.

In some embodiments, applicator 106 has a length which is the same (e.g., with a difference of no more than 20 millimeters or no more than 10 millimeters) as the length of elongate needle 104, such that when applicator 106 is inserted into the inner channel of needle 104 and their handles are connected, the distal end of applicator 106 coincides (within 10 millimeters, or even within five millimeters) with the distal end of needle 104. In some embodiments, applicator 106 is longer than needle 104 by the length of the handle of needle 104 (within five millimeters).

In other embodiments, applicator 106 is longer than elongate needle 104 by an extent such that when their handles are connected applicator 106 extends beyond the end of needle 104 by at least 2 centimeters, at least 5 centimeters or even at least 8 centimeters. Optionally, the distal end of applicator 106 comprises a stiff material, such as nitinol, which can penetrate a tumor with the use of a sharp needle. Insertion of applicator 106 on its own into the tumor has the advantage of causing an entrance hole with a smaller diameter. In some embodiments, the distal end of applicator 106 is pre-shaped with a specific angle, to reach a specific location and/or orientation, which is harder to access with the needle.

The elongate tubes of needle 104 and applicator 106 have a length of at least 20 centimeters, at least 50 centimeters, at least 80 centimeters, at least 100 centimeters, at least 120 centimeters or even at least 150 centimeters. Stylet 108 is generally slightly longer than applicator 106 so that it can push all seeds 110 out of the distal end of the applicator.

Figure 2:
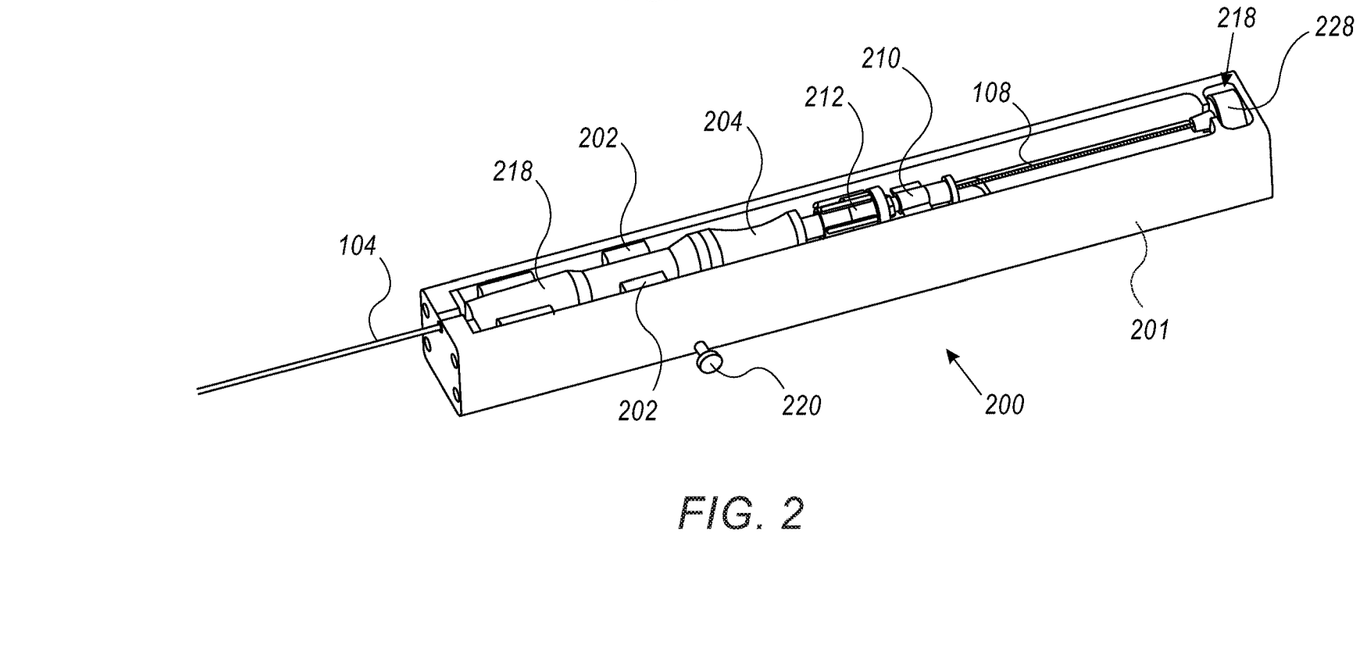
FIG. 2 is a schematic illustration of a proximal end of a needle in a seed dispensing unit, in accordance with an embodiment of the present invention.

FIG. 2 is a schematic illustration of a proximal end of needle 104 in a seed dispensing unit 200, in accordance with an embodiment of the invention. Seed dispensing unit 200 is designed to allow a human user to controllably move the needle 104 and applicator 106 relative to the stylet 108 in order to dispense seeds 110. As explained in detail below, seed dispensing unit 200 includes a casing 201, which receives a needle handle 204 together with a sheath handle 218 in a first end and a stylet handle 228 in an opposite end, and allows the user to controllably push the handles relative to each other. Seed dispensing unit 200 is designed, in some embodiments, to easily retract needle 104 and applicator 106 relative to stylet 108 by the length of a single seed, in order to release the seed. In some embodiments, before loading needle handle 204 into seed dispensing unit 200, a proximal handle 210 of applicator 106 is connected to needle handle 204, for example by a swivel Luer lock 212.

In some embodiments, in one end, seed dispensing unit 200 includes lips 202 of a slidable needle holder 252, designed to hold needle handle 204, and on an opposite end, seed dispensing unit 200 includes a compartment 218 designed to receive a proximal handle 228 of stylet 108.

Seed dispensing unit 200 is optionally sufficiently long to receive the needle handle 204, applicator handle 210 and stylet handle 228, along with an empty area between applicator handle 210 and stylet handle 228 of the length of several (e.g., at least 2, at least 3, at least 4 or even at least 5) seeds 110, so that needle handle 204 together with applicator handle 210 may be retracted in a manner releasing the seeds.

Applicant has found that the release of seeds 110 by retraction of needle 104 and/or applicator 106 has advantages over pushing the seeds forward by stylet 108. Using release by retraction, the entrance into the tumor is performed by a distal end of needle 104 and/or applicator 106 which may be more adapted for maneuver, for example by having a sharp end, than the seeds 110. Also, the precise location of the seeds may be determined before the release of the seeds, and if necessary, the distal end of the applicator 106 may be repositioned before the seed is released.

It is noted, however, that in some embodiments, instead of using retraction, stylet 108 is pushed forward to push the seeds 110 out of the needle and/or applicator 106 into the tumor.

FIG. 2 also shows a ratchet release button 220 which allows resetting of the needle holder 252 (FIG. 3) position in relation to seed dispensing unit 200, as discussed below with reference to FIG. 8.

Figures 3, 4:
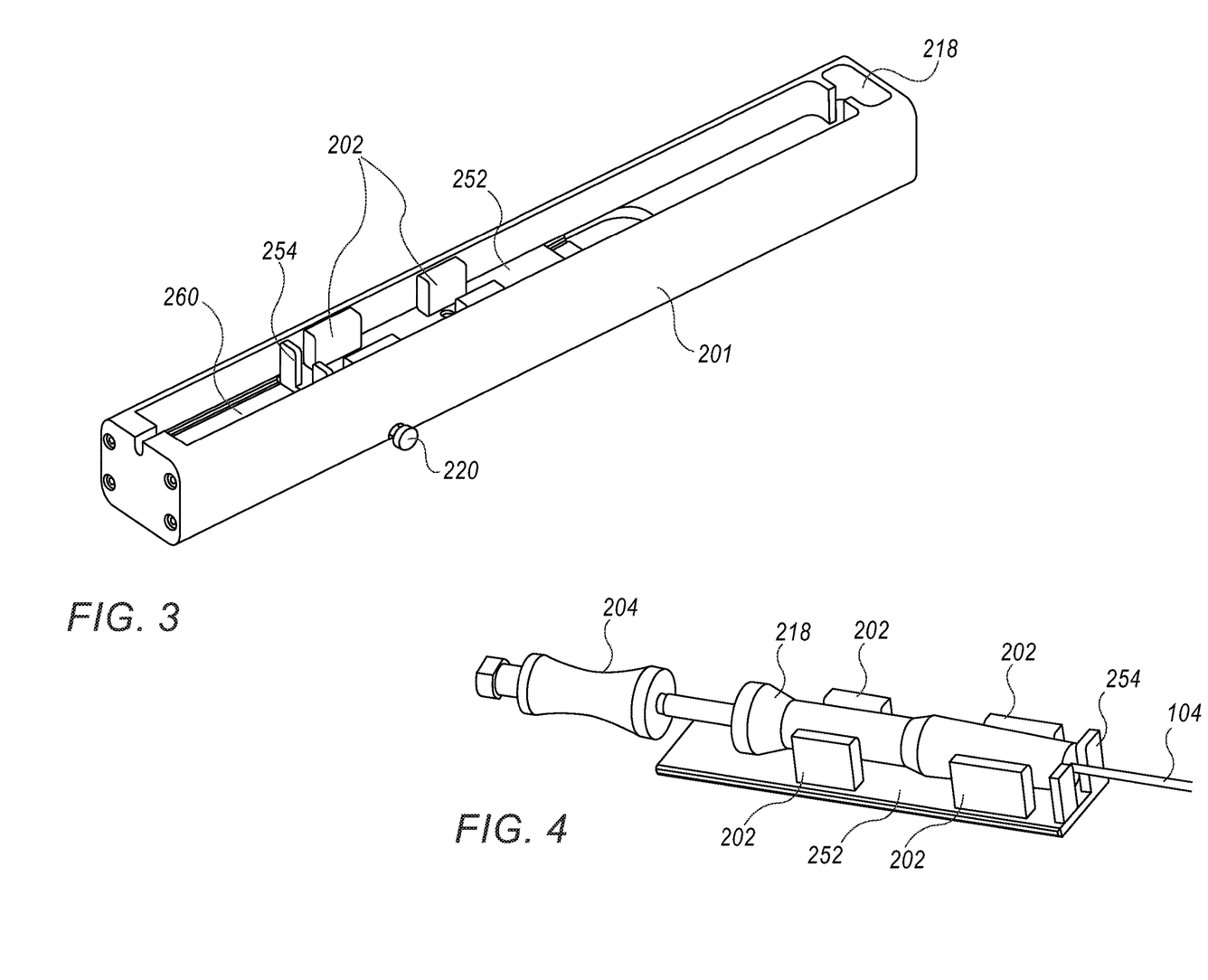
FIG. 3 is a schematic illustration of the seed dispensing unit of FIG. 2, without the needle handle, in accordance with an embodiment of the invention.
FIG. 4 is a schematic illustration of a cradle needle holder holding a needle handle, in accordance with an embodiment of the invention.

FIG. 3 is a schematic illustration of seed dispensing unit 200 without needle handle 204, in accordance with an embodiment of the invention. Seed dispensing unit 200 optionally includes a needle holder 252, also referred to herein as a cradle, having lips 202 intended to grasp needle handle 204 (FIG. 2). Needle holder 252 is optionally designed to slide relative to casing 201. Optionally, needle holder 252 slides on a slide frame 260 located on the backwall of casing 201 inside the casing. The functionality of slide frame 260 is discussed below with reference to FIG. 7.

Reference is also made to FIG. 4, which is a schematic illustration of cradle needle holder 252 holding needle handle 204, without casing 201, in accordance with an embodiment of the invention. In some embodiments, cradle needle holder 252 is designed to hold a needle handle 204 of a specific size and shape. In other embodiments, cradle needle holder 252 can receive needle handles of a plurality of different lengths, for example by cradle needle holder 252 having a wall 254 on its long axis only on its distal end and not on its proximal end. Alternatively or additionally, cradle needle holder 252 can receive needle handles of a plurality of different widths and/or shapes, for example due to elasticity of lips 202 and/or adjustability of the distance between the lips 202 as mounted on the cradle needle holder 252. Alternatively or additionally, casing 201 replaceably receives cradle needle holder 252 and when an irregular needle handle 204 is used, the needle handle is supplied with a replacement cradle needle holder 252 which properly grasps the irregular needle handle 204.

Figure 5:
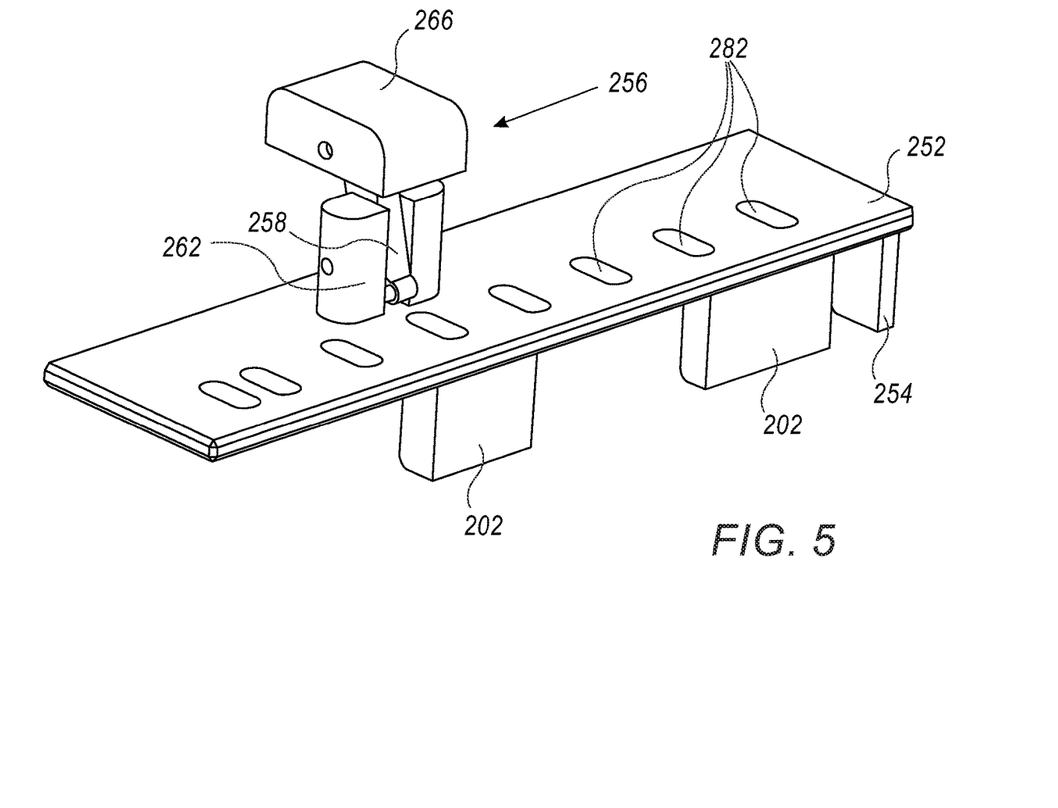
FIG. 5 is a schematic illustration of a cradle needle holder upside down, with a guide used to move the needle holder, in accordance with an embodiment of the invention.

FIG. 5 is a schematic illustration of cradle needle holder 252 upside down, with a guide 256 used to move the needle holder, in accordance with an embodiment of the invention. Guide 256 comprises a guide handle 266 located outside a back side of casing 201 and a guide base 262 connected to needle holder 252. A T-shaped rod 258 is optionally rotatably connected to both guide handle 266 and to guide base 262, in a manner which connects guide handle 266 to guide base 262, while allowing limited rotation of the rod, as discussed in detail below.

Figure 6:
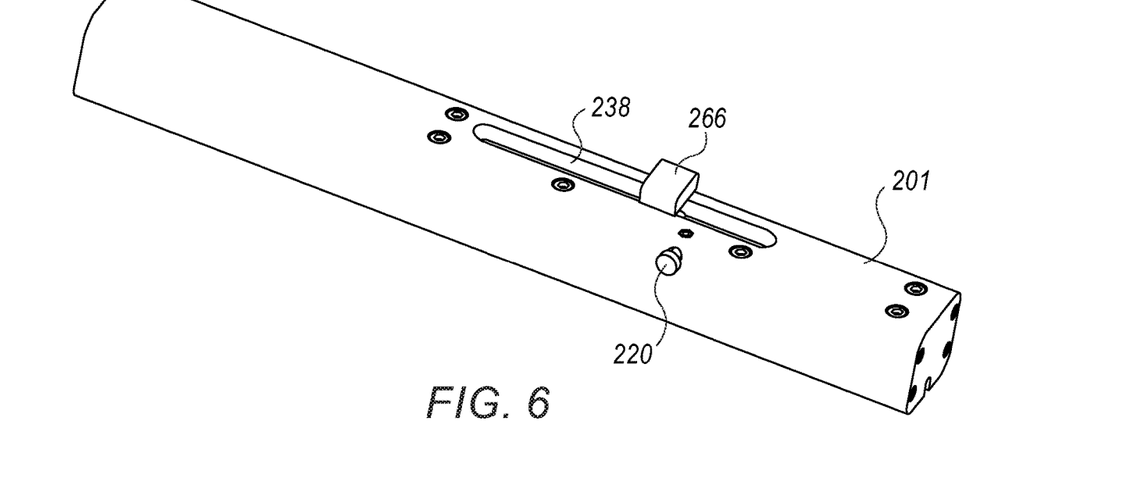
FIG. 6 is a schematic illustration of a back side of a casing of a seed dispensing unit, along with a guide handle, in accordance with an embodiment of the invention.

FIG. 6 is a schematic illustration of a back side of casing 201, along with guide handle 266, in accordance with an embodiment of the invention.

Guide handle 266 can be moved by an operator, for example, a physician, to release seeds 110 (FIG. 1). In some embodiments, casing 201 has a slot 238 in its back side to allow the sliding of rod 258 (FIG. 5).

Figure 7:
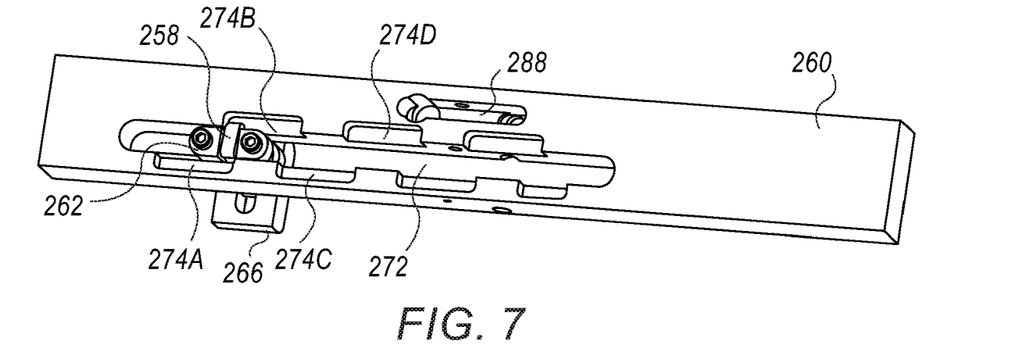
FIG. 7 is a schematic illustration of a slide frame and a corresponding guide, in accordance with an embodiment of the invention.

FIG. 7 is a schematic illustration of slide frame 260 and guide 256, in accordance with an embodiment of the invention. Slide frame 260 comprises a central slot 272, which corresponds to slot 238 in casing 201 (FIG. 6) and allows guide 256 to slide along the casing, thus moving needle holder 252 backwards and releasing seeds from a distal end of elongate needle 104.

In some embodiments, slide frame 260 additionally defines side slots 274 (labelled 274A, 274B, 274C, 274D) on both sides of central slot 272. Each side slot 274 optionally has a length of one seed. Side slots 274 are distributed alternately along the length of central slot 272, with a slight overlap of about the width of T-shaped rod 258. As shown, side slots 274 are only partially carved in slide frame 260. In other embodiments, side slots 274 are carved through the entire thickness of slide frame 260. Alternatively to side slots 274 having a length of a single seed, one or more slots, possibly even all the slots, have a length of multiple seeds, for example two seeds. In one embodiment, the first side slot 274A has a double length for release of two seeds and the remaining slots are designed for release of a single seed. Further alternatively, some or all of the slots 274 have a length shorter than the length of seeds 110, and in order to release a seed needle holder 252 is retracted for the length of a plurality (e.g., two or three) of slots.

Guide 256 is designed such that the T-head of T-shaped rod 258 does not fit in central slot 272 and needs to have one of the edges of the T-head in one of side slots 274. Therefore, in order to slide along slide frame 260, an edge of T-shaped rod 258 needs to be located in a side slot 274 which allows the sliding. At first, an edge of T-shaped rod 258 is located in side slot 274A. In this position, guide 256 can slide the length of a single seed 110 and thus release a seed. Thereafter, guide handle 266 is optionally pushed orthogonally to the sliding direction, so that an edge of T-shaped rod 258 enters side slot 274B. In this state, guide 256 can slide the length of another seed 110. Guide handle 266 is then pushed orthogonally to the sliding direction, in a direction opposite to its previous push, so that an edge of T-shaped rod 258 enters side slot 274C. This process may continue to release any number of seeds 110 from within applicator 106.

It is noted that while the above embodiment describes a specific mechanism for limiting the sliding of needle holder 252, any other suitable mechanism for sliding in steps of the length of seeds 110 may be used, such as ball plungers, as discussed below with reference to FIGS. 10A-12B.

Figure 8A:
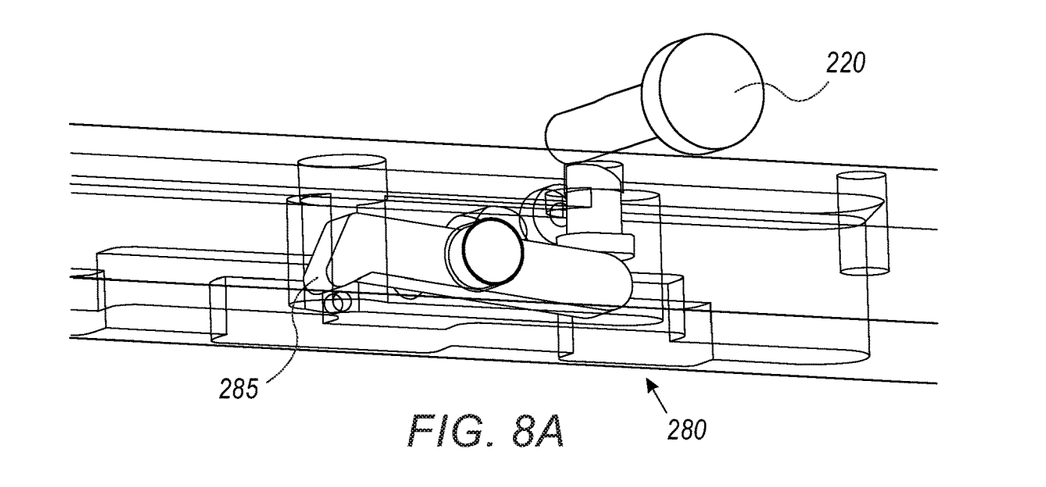
FIGS. 8A and 8B are schematic illustrations of a ratchet mechanism, in accordance with an embodiment of the invention.

FIG. 8A is a schematic illustration of a ratchet mechanism 280 within casing 201, in accordance with an embodiment of the invention.

Figure 8B:
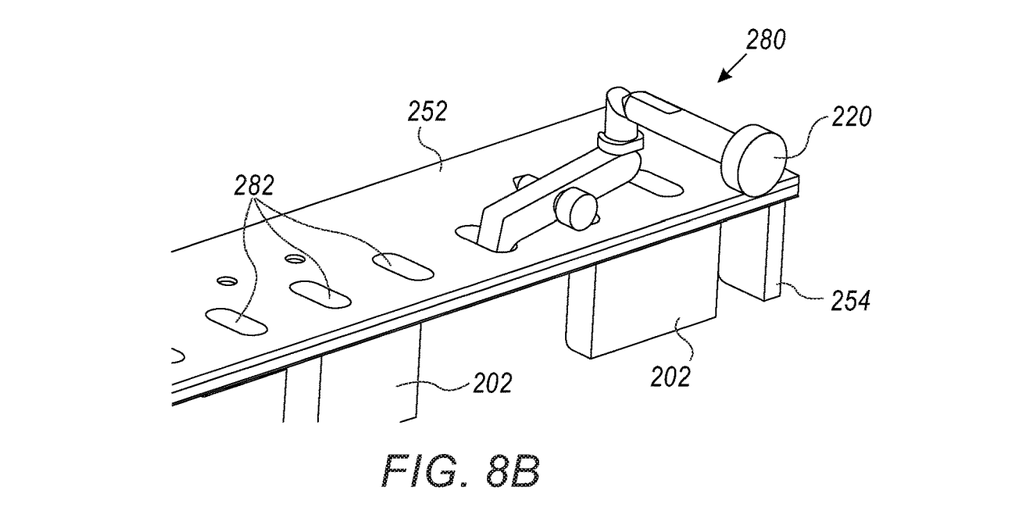

FIG. 8B is a schematic illustration of an interaction between ratchet mechanism 280 and needle holder 252, in accordance with an embodiment of the invention.

Optionally, ratchet mechanism 280 restricts the movement of cradle needle holder 252. Optionally, needle holder 252 defines holes 282 along its length, and ratchet mechanism 280 comprises a member 284 having a bulging head 285 configured to fit into holes 282. In some embodiments, a spring urges bulging head 285 against the back of cradle needle holder 252, such that when the bulging head 285 is above a hole 282, bulging head 285 fits into the hole and prevents or limits movement of needle holder 252. In order to release bulging head 285, a user may press ratchet release button 220. Holes 282 are optionally defined at points corresponding to the ends of side slots 274, so that once needle holder 252 is moved the length of a seed, the needle holder 252 cannot move backwards without the user pressing button 220. In order to release another seed, the user moves guide 256 sideways in a manner which allows further movement and prevents backward movement by a current side slot 274. Then, the user presses button 220 to remove bulging head 285 from the hole 282 in which it was located and allow further movement.

In some embodiments, the fitting of bulging head 285 in a hole 282 prevents both forward and backward movement, and movement is allowed only by pressing button 220. Alternatively, the fitting of bulging head 285 in a hole 282 prevents backward movement, but forward movement is allowed, for example, by holes 282 having a forward slope which allows exit of bulging head 285 with forward movement.

Figure 9:
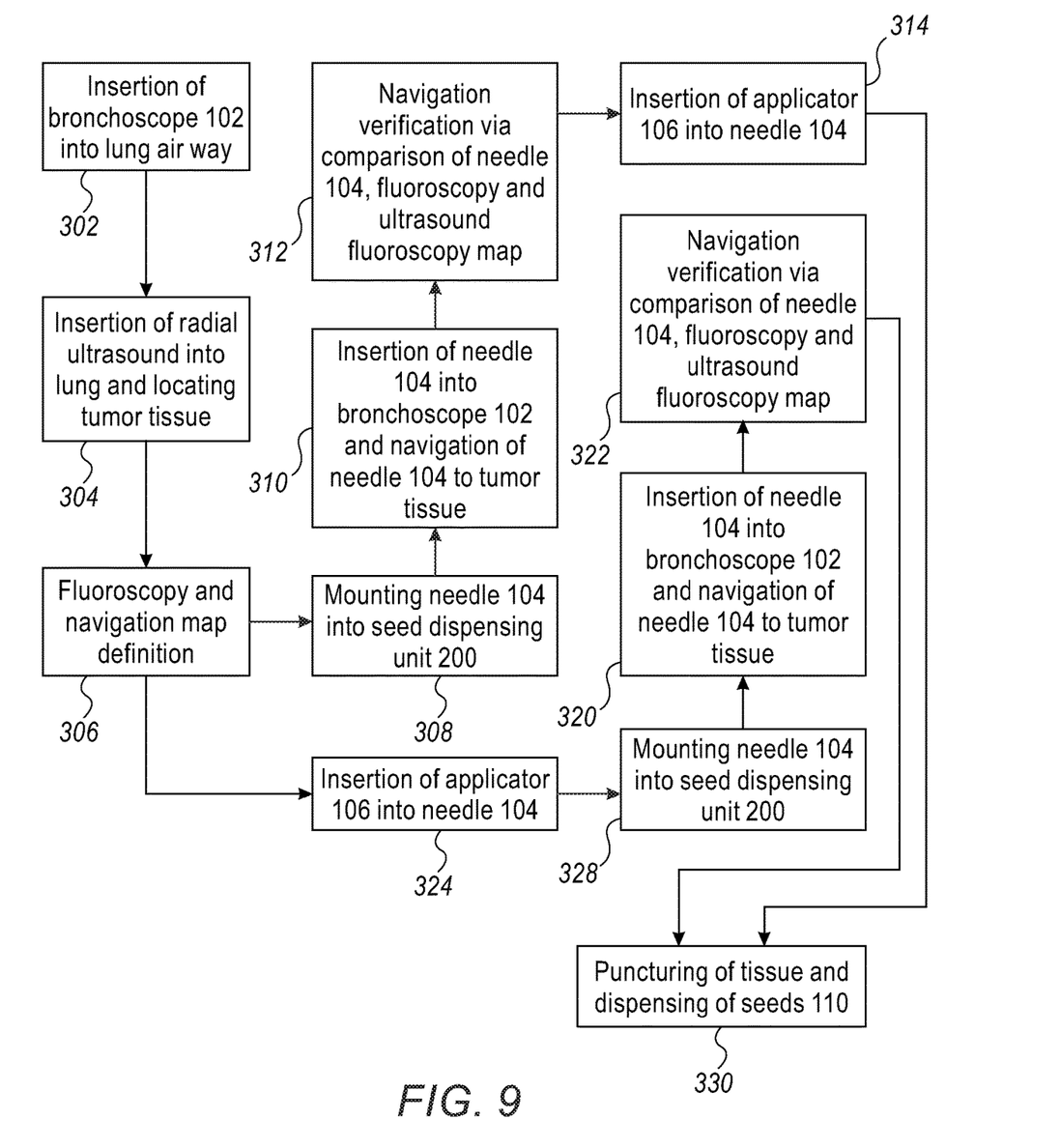
FIG. 9 is a flowchart of acts performed in implanting radiotherapy seeds in a tumor of a patient, in accordance with embodiments of the invention.

FIG. 9 is a flowchart of acts performed in using system 100 to implant radiotherapy seeds 110 in a tumor of a patient, in accordance with embodiments of the invention.

The method of FIG. 9 optionally starts with inserting endoscope 102 into the patient (302). In some embodiments, a radial ultrasound is also inserted (304) into the patient in order to locate the tumor and direct a distal end of bronchoscope 102 to the tumor. Alternatively or additionally, any other method may be used to direct endoscope 102 to the tumor, such as fluoroscopy (306).

In some embodiments, needle 104 is inserted into endoscope 102, before applicator 106 is inserted into needle 104. In these embodiments, needle 104 is inserted into a proximal end of endoscope 102 and is led through the endoscope to its distal end (310). Optionally, needle 104 is inserted into the proximal end of endoscope 102 from seed dispensing unit 200. After the location of needle 104 is verified (312), applicator 106 is inserted into a proximal end of the needle outside the patient and is led to the tip of the needle 104. The needle then punctures (330) the tissue and applicator 106, under control of a user manipulating seed dispensing unit 200, inserts the seeds into the tumor.

In other embodiments, needle 104 is inserted into the patient with applicator 106 already preloaded therein (324). The needle 104 is mounted (328) into seed dispensing unit 200 with applicator 106 already therein and together the needle and the applicator are led (320) through endoscope 102 to the tumor. The location of needle 104 relative to the tumor is verified (322) and the needle then punctures (330) the tissue and the seeds are inserted to the tumor by pushing stylet 108 from seed dispensing unit 200.

It is noted that the acts of FIG. 9 are not necessarily performed in the order shown and/or described and acts may be performed in other orders and/or one or more acts are performed concurrently. For example, in some embodiments, applicator 106 is inserted to needle 104 only after the needle punctures the tumor. The imaging to verify the location of the needle and applicator may be performed at any time deemed necessary, optionally continuously.

In accordance with the above embodiments, seeds 110 are delivered into the tumor within four channels:
1) outer endoscope 102
2) needle sheath 118
3) needle 104
4) applicator 106

While seeds 110 could be delivered in only two channels (e.g., endoscope and needle), the use of an extra channel (e.g., applicator 106) provides more flexibility to the delivery process. The applicator 106 provides extra protection to seeds 110 and prevents them from rubbing against the inner walls of needle 104, so that the radionuclides of seeds 110 do not rub off due to friction.

Figures 10A, 10B:
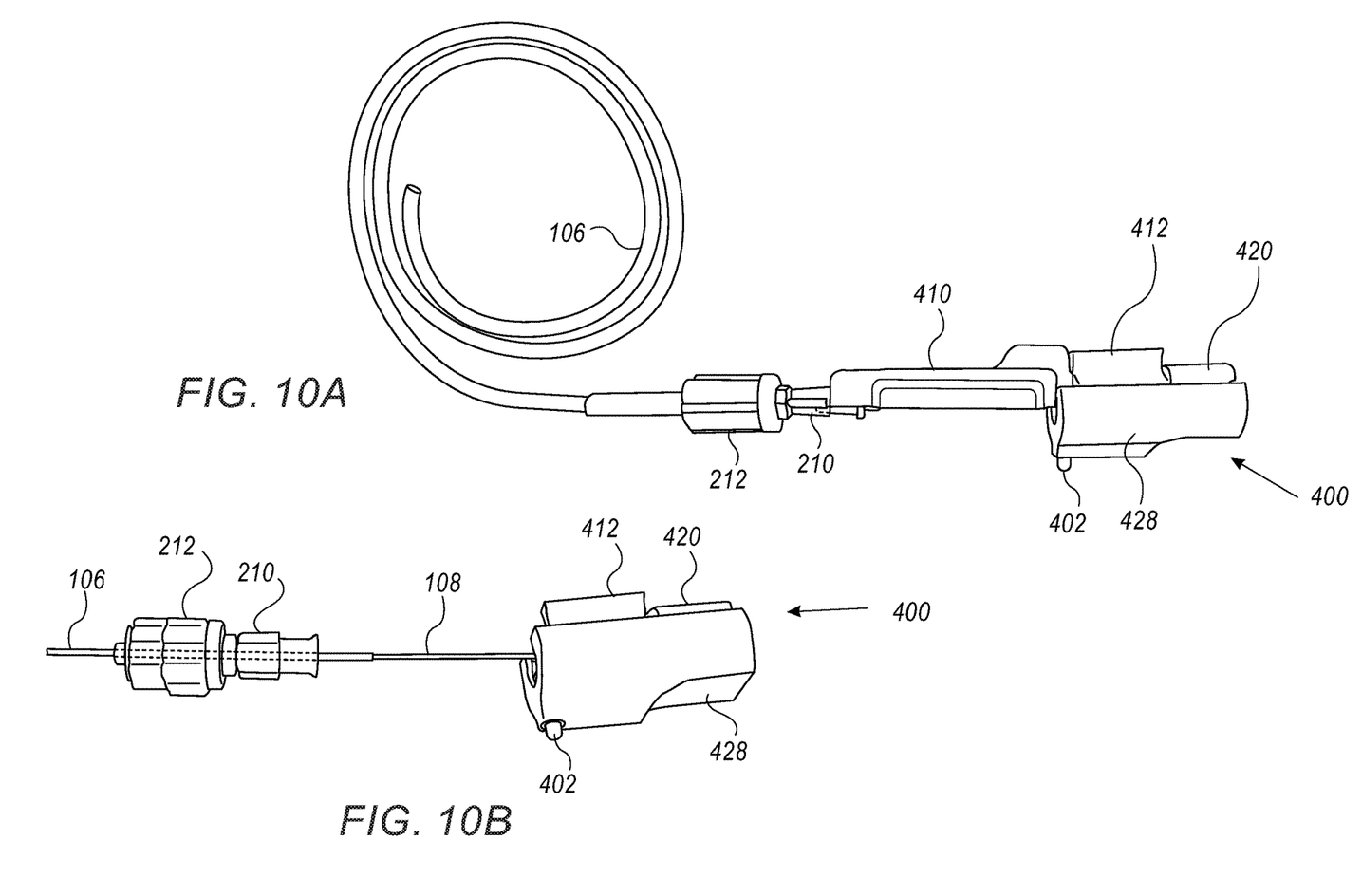
FIG. 10A is a schematic illustration of an applicator kit, in accordance with an embodiment of the present invention.
FIG. 10B is a schematic illustration of a proximal end of the applicator kit of FIG. 10A, with a first fixation element removed, in accordance with an embodiment of the present invention.

FIG. 10A is a schematic illustration of an applicator kit 400, in accordance with an embodiment of the present invention.

FIG. 10B is a schematic illustration of a proximal end of applicator kit 400, with a first fixation element 410 (FIG. 10A) removed, in accordance with an embodiment of the present invention.

Applicator kit 400 comprises an applicator 106 which is loaded with one or more radioactive seeds (FIG. 1) near its distal end, and an applicator handle 210 with a swivel Luer lock 212 for connecting to needle handle 204, at its proximal end. Applicator kit 400 further includes a stylet 108 within applicator 106, which has a stylet handle 420 mounted on a stylet carrier 428. Optionally, stylet carrier comprises on its bottom a ball plunger 402 to lock the stylet at a desired location within casing 454, as discussed hereinbelow. In addition, kit 400 includes a first fixation element 410 and a second fixation element 412. As discussed above, applicator 106 is designed for delivery with an elongate needle 104 (FIG. 1). Elongate needle 104 may be supplied together with applicator kit 400 or may be provided separately.

Figure 11A:
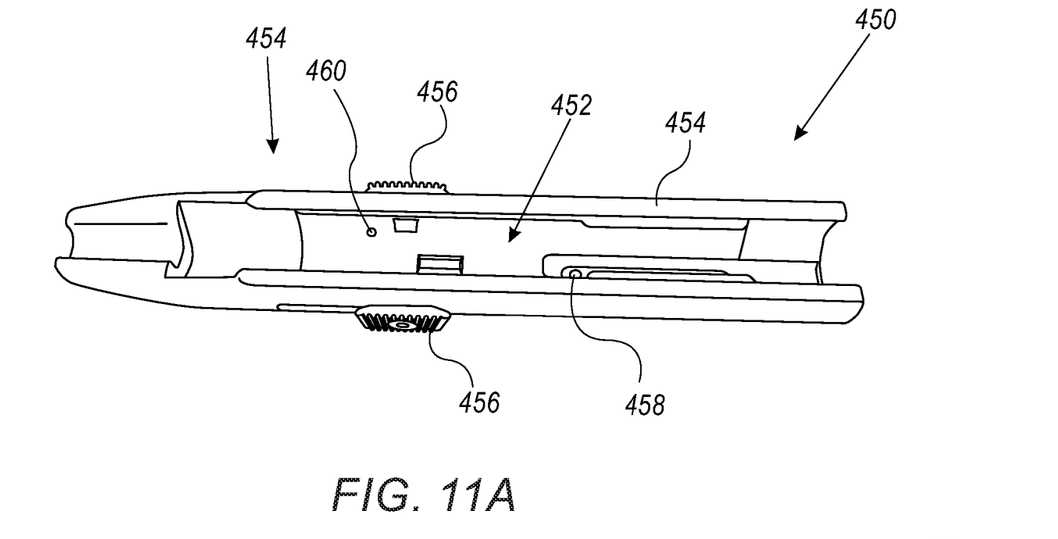
FIG. 11A is a schematic top view of a seed dispensing unit, in accordance with an embodiment of the present invention.

FIG. 11A is a schematic top view of a seed dispensing unit 450, in accordance with an embodiment of the present invention.

Figure 11B:
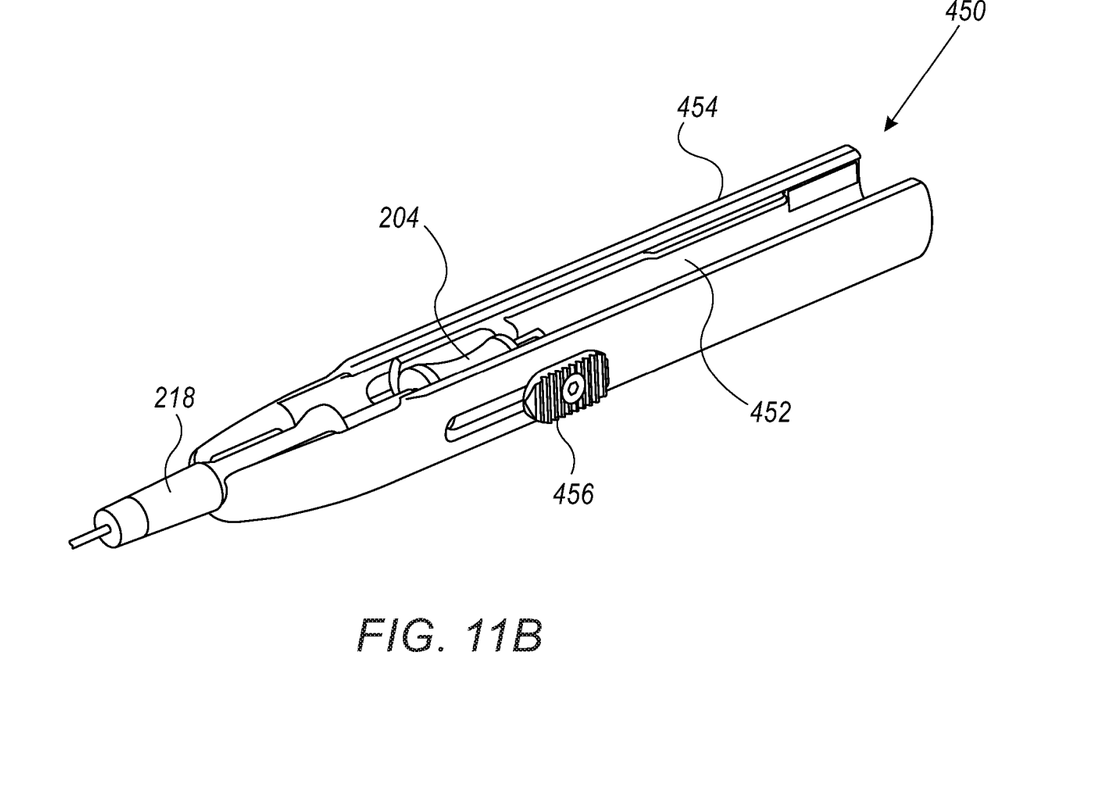
FIG. 11B is a schematic side view of the seed dispensing unit of FIG. 11A, with a needle handle and sheath handle mounted therein.

FIG. 11B is a schematic side view of the seed dispensing unit 450 of FIG. 11A, with needle handle 204 and sheath handle 218 mounted therein. Seed dispensing unit 450 comprises a casing 454 designed to receive sheath handle 218 on one end, and stylet carrier 428 (FIG. 10A) on the other end. Unlike seed dispensing unit 200, which receives stylet handle 228 (FIG. 2) in a fixed location, casing 454 is designed to allow stylet carrier 428 to slide within the casing. Seed dispensing unit 450 further includes a slider 452 designed to receive needle handle 204 and slide with it along casing 454. Sliding grippers 456 are used by a physician or other medical professional to slide slider 452. In some embodiments, casing 454 has on its side wall one or more ball plungers 460 and slider 452 has corresponding one or more notches, designed to stop the sliding at predetermined distances, for example of the size of a single seed. A notch 458 is defined on the bottom of casing 454, in which ball plunger 402 fits to lock stylet carrier 428, as discussed below.

Figure 12A:
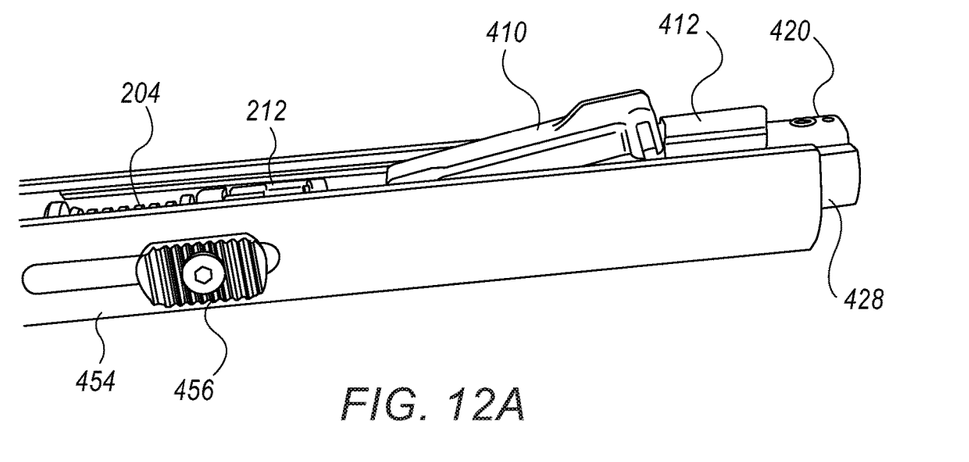
FIGS. 12A and 12B are side and top views, respectively, of the seed dispensing unit of FIG. 11A, with a stylet carrier mounted therein, in accordance with an embodiment of the present invention.
Figure 12B:
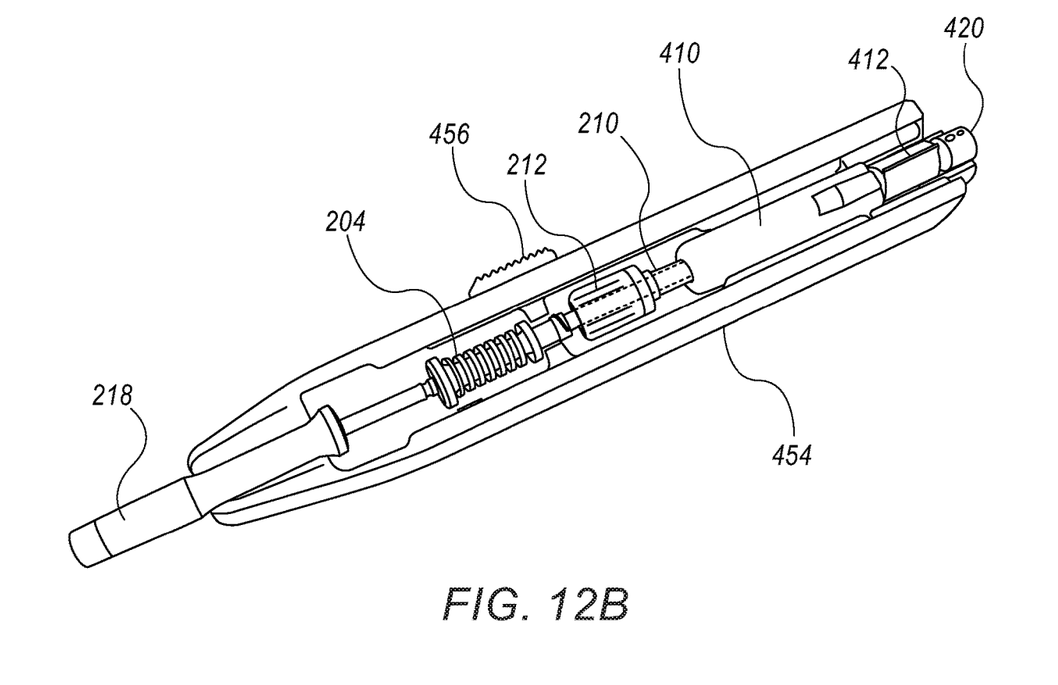

FIGS. 12A and 12B are side and top views, respectively, of casing 454 with stylet carrier 428 mounted therein, in accordance with an embodiment of the present invention.

In operation, in accordance with some embodiments, applicator 106 is mounted into elongate needle 104, and applicator handle 210 is attached to needle handle 204. Sheath handle 218 is placed on one side of casing 454, needle handle 204 is mounted into slider 452 and stylet carrier 428 is slid onto the other side of casing 454. In this state, with first fixation element 410 and second fixation element 412 in place between applicator handle 210 and stylet handle 420, the distal tip of elongate needle 104 is brought in proximity to a tumor in which seeds 110 are to be implanted. Generally, during delivery of the tip of elongate needle 104 to the tumor, its sharp end is retracted into sheath 118, such that there is a gap between sheath handle 218 and needle handle 204.

In preparation for implanting the seeds 110, first fixation element 410 is removed from casing 454. In order to push needle 104 into the tumor, sliding grippers 456 are slid distally along with slider 452, thus moving needle handle 204, applicator handle 210 and stylet carrier 428 along with stylet handle 420, towards sheath handle 218. After a penetration distance suitable for a predetermined number of seeds, ball plunger 402 at the bottom of stylet carrier 428 locks into notch 458, preventing movement of stylet carrier 428. To release the seeds, sliding grippers 456 are slid proximally, thus pulling needle 104 and applicator 106 distally, while style 108 does not move, because stylet carrier 428 is locked in place. The stylet 108, therefore does not allow the seeds to retract with needle 104 and they remain in the tumor.

Optionally, in retracting sliding grippers 456, after each seed length of retraction, a side wall ball plunger 460 fits into a corresponding notch, indicating to the operator that a seed was released. After release of the predetermined number of seeds, second fixation element 412 may be removed to allow sliding of stylet handle 420 distally on stylet carrier 428, so as to push further seeds within applicator 106 distally. Then, after positioning the distal end of sheath 118 at a suitable location relative to a tumor (the same tumor or a different tumor), the operation of inserting the needle 104 into the tumor and retracting the needle is repeated, to implant further seeds.

In some embodiments, the predetermined number of seeds which can be implanted after removal of each of first fixation element 410 and second fixation element 412, is two. In other embodiments, however, the predetermined number of seeds is greater than two, being, for example, three or four. Alternatively, the predetermined number of seeds is one. Although in the above description, applicator kit 400 has only two fixation elements 410 and 412, in other embodiments an applicator kit has additional fixation elements so that more seeds can be implanted using the applicator kit.

Endoscope 102 may be any suitable type of endoscope, including a bronchoscope, anoscope, arthroscope, colonoscope, colposcope, cystoscope, esophagoscope, gastroscope, laparoscope, laryngoscope, neuroendoscope, proctoscope, sigmoidoscope or thoracoscope. While the above description relates specifically to an endoscope, in some embodiments of the invention, needle 104 and applicator 106 carrying one or more seeds 110 are inserted into a patient through other types of medical probes, which include or do not include viewing apparatus. In still other embodiments, needle 104 is inserted into the patient directly without the use of a leading endoscope or medical probe.

CONCLUSION

It will be appreciated that the above described methods and apparatus are to be interpreted as including apparatus for carrying out the methods and methods of using the apparatus. It should be understood that features and/or steps described with respect to one embodiment may sometimes be used with other embodiments and that not all embodiments of the invention have all of the features and/or steps shown in a particular figure or described with respect to one of the specific embodiments. Tasks are not necessarily performed in the exact order described.

It is noted that some of the above described embodiments may include structure, acts or details of structures and acts that may not be essential to the invention and which are described as examples. Structure and acts described herein are replaceable by equivalents which perform the same function, even if the structure or acts are different, as known in the art. The embodiments described above are cited by way of example, and the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Therefore, the scope of the invention is limited only by the elements and limitations as used in the claims, wherein the terms "comprise," "include," "have" and their conjugates, shall mean, when used in the claims, "including but not necessarily limited to."

The invention claimed is:

1. An applicator for delivery of radiotherapy seeds to a tumor of a patient through an elongate needle, wherein the elongate needle comprises a needle handle and a needle tube having a given length for insertion into the patient, comprising:
   an elongate applicator tube designed to pass through the elongate needle, wherein the elongate applicator tube defines an internal channel which receives one or more radiotherapy seeds;
   an applicator handle configured to be attached to the needle handle;
   a stylet within the elongate applicator tube; and
   a seed dispensing unit configured to grasp the applicator handle and a handle of the stylet, in a manner which allows movement of the applicator handle relative to the stylet handle, such that the stylet pushes a seed out of the distal end of the elongate applicator tube,
   wherein the elongate applicator tube is longer than the elongate needle, and
   wherein the seed dispensing unit comprises:
      a casing configured to grasp the stylet handle; and
      a slidable holder configured to couple with the applicator handle and slide relative to the casing.

2. The applicator of claim 1, wherein the elongate applicator tube has a flexibility which is not suitable for insertion into a patient, but can pass through an inner channel of the elongate needle, when the elongate needle is in the patient.

3. The applicator of claim 1, wherein the elongate applicator tube has a length such that when the applicator handle is attached to the needle handle, a distal end of the elongate applicator tube is in close proximity to a distal end of the elongate needle.

4. The applicator of claim 1, wherein the elongate applicator tube has a length of at least 20 centimeters.

5. The applicator of claim 1, wherein the seed dispensing unit is configured to retract the applicator handle while the handle of the stylet is held in place.

6. The applicator of claim 5, wherein the elongate applicator tube has a length of at least 50 centimeters.

7. The applicator of claim 1, wherein the seed dispensing unit comprises a guide handle which when moved, by a user, along an axis of the elongate applicator tube, moves the applicator handle relative to the stylet handle.

8. The applicator of claim 7, wherein the seed dispensing unit is configured to limit movement of the guide handle along the axis of the elongate applicator tube in a single stroke, to the length of a single seed.

9. The applicator of claim 8, wherein the seed dispensing unit is configured to require sideways movement of the guide handle, to allow further movement of the guide handle along the axis of the elongate applicator tube, after movement of the length of a single seed.

* * * * *